US00PP26035P3

(12) United States Plant Patent
Dobres

(10) Patent No.: US PP26,035 P3
(45) Date of Patent: Nov. 3, 2015

(54) ***CARYOPTERIS* PLANT NAMED 'NOVACARGOL'**

(50) Latin Name: *Caryopteris hybrida*
Varietal Denomination: Novacargol

(71) Applicant: CP DELAWARE, INC., Wilmington, DE (US)

(72) Inventor: Michael S. Dobres, Philadelphia, PA (US)

(73) Assignee: CP DELAWARE, INC., Wilmington, DE (US)

( * ) Notice: Subject to any disclaimer, the term of this patent is extended or adjusted under 35 U.S.C. 154(b) by 181 days.

(21) Appl. No.: 13/998,744

(22) Filed: Dec. 3, 2013

(65) Prior Publication Data

US 2015/0156941 P1 Jun. 4, 2015

(51) Int. Cl.
*A01H 5/02* (2006.01)

(52) U.S. Cl.
USPC ..... Plt./226

(58) Field of Classification Search
USPC ..... Plt./226, 263.1
CPC ..... A01H 5/02; A01H 5/00
See application file for complete search history.

*Primary Examiner* — Kent L Bell
(74) *Attorney, Agent, or Firm* — Buchanan Ingersoll & Rooney PC

(57) ABSTRACT

A new and distinct *Caryopteris* plant is provided which is the product of a controlled breeding program followed by selection. Attractive lilac-colored flowers in a verticillaster arrangement are formed on a substantially uniform basis. The growth habit is compact and ascending with strong branching. Attractive light green to golden foliage is displayed. During observations to date, the golden coloration of the foliage has tended to be more pronounced during cooler growing conditions. The plant is well suited for providing attractive colorful ornamentation in the landscape.

1 Drawing Sheet

Figure 1:
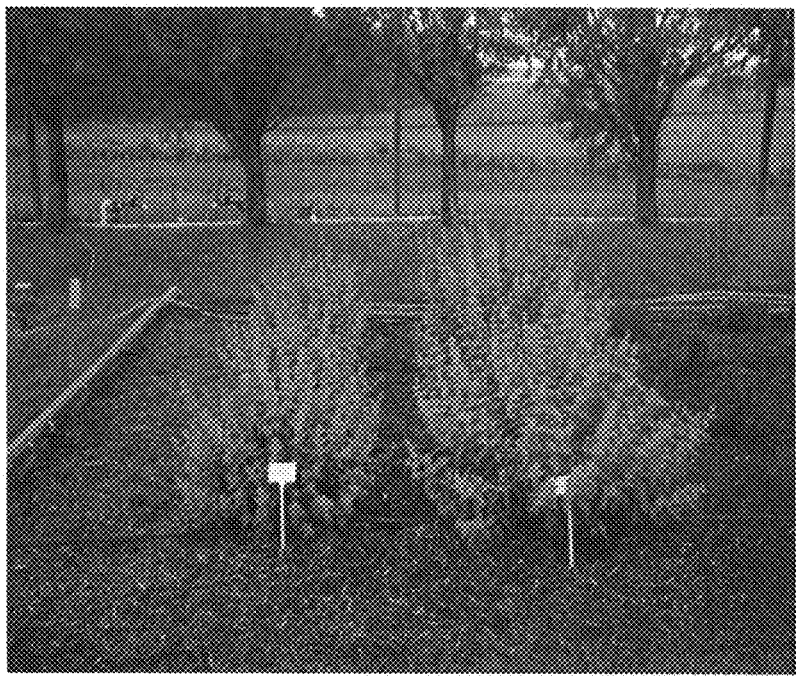

Botanical/commercial classification: *Caryopteris hybrida*/ Blue Mist Shrub.

Varietal denomination: cv. Novacargol.

SUMMARY OF THE INVENTION

*Caryopteris* plants commonly are recognized to be a member of the Laminaceae family and are sometimes identified by the Blue Mist and Bluebeard common names.

A new *Caryopteris hybrida* plant of the present invention was formed at West Grove, Pa., U.S.A., by artificial pollination wherein two parents were crossed which previously had been studied in the hope that they would contribute the desired characteristics. The female parent (i.e., the seed parent) was the *Caryopteris* × *clandonensis* 'Durio' variety (U.S. Plant Pat. No. 16,913). Such female parent sometimes bears the PINK CHABLIS designation. The male parent (i.e., pollen parent) was a *Caryopteris incana* 'Jason' variety (U.S. Plant patent application Ser. No. 10/878,606—now abandoned) which is understood to be native from Japan to northwest China. The 'Jason' variety sometimes is designated SUNSHINE BLUE. The parentage of the new plant can be summarized as follows:

'Durio' 'Jason'

*Caryopteris* × *clandonensis* × *Caryopteris incana.*

The seeds resulting from the pollination were sown and small plants were obtained which were physically and biologically different from each other. Selective study resulted in the identification of a single plant of the new variety.

It has been found that the new *Caryopteris* plant of the present invention displays the following combination of characteristics:

(a) displays a compact ascending growth habit with strong branching,
(b) forms on a substantially uniform basis attractive lilac-colored flowers in a verticillaster arrangement,
(c) displays attractive light green to golden foliage,
(d) has been observed to be hardy to U.S.D.A. Hardiness Zone No. 7, and
(e) is well suited for providing attractive ornamentation in the landscape.

The new plant of the present invention can be grown to advantage to provide distinctive colorful ornamentation in parks and gardens.

The new plant can be readily distinguished from its ancestors and all other *Caryopteris* plants known to its originator. More specifically, the 'Durio' female parent displays pink-colored flowers unlike the lilac-colored flowers of the new plant. The 'Jason' male parent displays a more open and less compact growth habit. The new variety also can be distinguished from the 'Lisaura' variety (U.S. Plant Pat. No. 20,608) through the display of a smaller more compact and less open growth habit. The 'Lisaura' variety sometimes bears the HINT OF GOLD designation.

Asexual reproduction of the new plant at West Grove, Pa., U.S.A., through the use of terminal cuttings has demonstrated that the distinctive characteristics are reliably transmitted from one generation to another. Accordingly, the new plant can be asexually reproduced in a true-to-type manner. The plant readily can be asexually reproduced via softwood and semi-hardwood cuttings.

The new plant initially was designated X01515-9-1 and subsequently has been named 'Novacargol'. The plant will be marketed under the GOOD AS GOLD trademark

BRIEF DESCRIPTION OF THE PHOTOGRAPHS

The accompanying photographs show as nearly true as it is reasonably possible to make the same in color illustrations of this character, typical specimens of the new variety. The plants are shown while growing during September 2012 in the ground outdoors at West Grove, Pa., U.S.A. The plants had been asexually reproduced through the use of terminal cuttings and were growing in full sun.

FIG. 1 illustrates at an age of approximately one year on the left a row of typical plants of the new variety and on the right a row of typical plants of the 'Lisaura' variety under the same growing conditions. It will be observed that the growth habit of the new variety is more compact and less open than that of the 'Lisaura' variety. The new variety displays a height of approximately 22 inches and a width of approximately 36 inches on average. The 'Lisaura' variety displays a height of approximately 33 inches and a width of approximately 48 inches on average.

Figure 2:
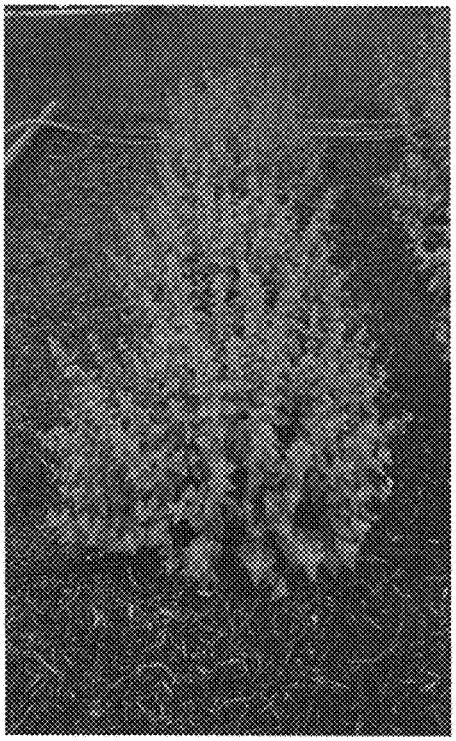

FIG. 2 illustrates a closer view of the row of plants of the new variety wherein the attractive lilac-colored flowers are uniformly borne.

DETAILED BOTANICAL DESCRIPTION

The following is a detailed description of the new plant of the present invention which generally was prepared while observing one-year-old plants growing in the ground outdoors in natural light during September 2012 at West Grove, Pa., U.S.A. Color terminology is in accordance with The R.H.S. Colour Chart (1995 or equivalent) of The Royal Horticultural Society, London, England, except when general color terms are used which are to be accorded their customary dictionary significance are used.

Type: Herbaceous perennial for garden decoration and general landscape usage.

Botanical classification: *Caryopteris hybrida.*

Parentage:

Caryopteris × clandonensis 'Durio'

×

Caryopteris incana 'Jason'

Asexual reproduction: Rooting of terminal cuttings.

Plant:

*Growth habit.*—Compact, ascending, and generally rounded at the top.

*Height.*—Approximately 22 inches on average.

*Width.*—Approximately 36 inches on average.

*Branching.*—Strong.

Foliage:

*Arrangement.*—Decussate.

*Length.*—Approximately 2 inches on average.

*Width.*—Approximately 1.5 inches on average.

*Shape.*—Lanceolate.

*Apex.*—Acute.

*Base.*—Rounded.

*Venation.*—Net-veined.

*Margin.*—Serrate.

*Texture.*—Glabrous on both surfaces.

*Color.*—Upper surface: near Yellow-Green Group 144A overlaid with a lighter Yellow-Green Group 151A to a golden coloration of near Yellow Group 7A. During observations to date, the golden coloration tends to be more pronounced under cooler growing conditions. Under surface: near Green Group 138B.

*Petiole.*—Length: approximately 6 mm on average. Diameter: approximately 2 mm on average. Texture: bears some short pubescence. Color (upper surface): near Green Group 139D. Color (under surface): near Green Group 139D.

Inflorescence:

*Flowering season.*—August to first frost.

*Arrangement.*—Verticillaster.

*Lastingness of blooms.*—Commonly approximately three days.

*Fragrance.*—None detected.

*Buds.*—Shape: ovoid. Length: approximately 3 mm on average. Width: approximately 2 mm on average. Color: near Purple-Violet Group 82D when tight.

*Flowers.*—Shape: zygomorphic with bilabiate petal arrangement. Diameter: approximately 3 mm on average. Depth: approximately 6 mm (total flower length). Funnel length: approximately 3 mm at opening. Funnel diameter: approximately 2 mm at opening. Petal number: five with four petals being fused to form an upper lip and one larger elongated petal on the lower lip thereby forming a funnel-shaped structure. Petal length: approximately 2 mm for the four fused petals on the upper lip, and approximately 4 mm for the larger elongated petal on the lower lip. Petal width: approximately 2 mm for the four fused petals and approximately 4 mm for the larger elongated petal on the lower lip. Petal apex: the four fused petals on the upper lip each have a aristulate apex, and the larger elongated petal on the lower lip commonly has a fringed border having a length of approximately 4 mm. Petal base: all petals are fused at the base. Petal margin: entire for four fused petals on the upper lip, and fringed for the elongated petal on the lower lip as previously indicated. Petal texture: glabrous. Petal color (inside throat): near White Group 155B when mature. Petal color (outside throat): near Violet-Blue Group 91B when mature. Stamen number: four per flower. Stamen disposition: exserted. Filament length: approximately 5 mm on average. Filament diameter: less than 1 mm on average. Filament color: near Violet-Blue Group 90C. Anther shape: bi-lobed. Anther length: approximately 1 mm on average. Anther diameter: less than 1 mm. Anther color: near Violet-Blue Group 90A. Pollen: no pollen detected during observations to date. Pistil number: one per flower. Pistil length: approximately 1 cm on average. Pistil disposition: erect. Style length: approximately 9 mm on average. Style diameter: less than 1 mm. Style color: Violet Group 84B. Stigma shape: bifid. Stigma length: less than 1 mm. Stigma color: Purple-Violet Group 80C. Ovary color: Yellow-Green Group 144A. Fruit/seeds: none detected during observations to date.

*Sepals.*—Number: five fused to form a calyx tube. Length: approximately 3 mm on average. Width: approximately 1 mm on average. Apex: acute. Base: fused. Margin: entire. Texture: commonly bear short pubescence. Color (upper surface): when fully open Green Group 138C. Color (under surface): when fully open Yellow-Green Group 144A.

*Pedicels*.—Length: approximately 2 mm on average. Diameter: less than 1 mm. Color: near Green Group 138C. Aspect: commonly approximately 45 degrees.

*Peduncle*.—Length: approximately 8 mm. Diameter: approximately 1 mm. Color: near Green Group 138C. Aspect: commonly approaching 90 degrees.

Development:

*Tolerance to diseases*.—During observations to date the plant is believed to be typical of the genus.

*Resistance to pests*.—During observations to date the plant is believed to be typical of the genus.

*Hardiness*.—Has been observed to be hardy to U.S.D.A. Hardiness Zone No. 7.

Plants of the new 'Novacargol' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Caryopteris* plant having the following combination of characteristics:

(a) displays a compact ascending growth habit with strong branching, (b) forms on a substantially uniform basis attractive lilac-colored flowers in a verticillaster arrangement, (c) displays attractive light green to golden foliage, (d) has been observed to be hardy to U.S.D.A. Hardiness Zone No. 7, and (e) is well suited for providing attractive ornamentation in the landscape;

substantially as illustrated and described.

* * * * *